(12) United States Patent
Murthi (10) Patent No.: US 11,523,796 B2
(45) Date of Patent: Dec. 13, 2022

(54) SYSTEM AND METHOD FOR ASSESSMENT OF CARDIAC STROKE VOLUME AND VOLUME RESPONSIVENESS

(71) Applicant: UNIVERSITY OF MARYLAND, BALTIMORE, Baltimore, MD (US)

(72) Inventor: Sarah B. Murthi, Lutherville, MD (US)

(73) Assignee: UNIVERSITY OF MARYLAND, BALTIMORE, Baltimore, MD (US)

(*) Notice: Subject to any disclaimer, the term of this patent is extended or adjusted under 35 U.S.C. 154(b) by 151 days.

(21) Appl. No.: 16/919,469

(22) Filed: Jul. 2, 2020

(65) Prior Publication Data
US 2020/0337672 A1 Oct. 29, 2020

Related U.S. Application Data

(62) Division of application No. 15/407,380, filed on Jan. 17, 2017, now Pat. No. 10,736,604.

(60) Provisional application No. 62/443,276, filed on Jan. 6, 2017, provisional application No. 62/278,717, filed on Jan. 14, 2016.

(51) Int. Cl.
*A61B 8/00* (2006.01)
*A61B 8/06* (2006.01)
*A61B 8/08* (2006.01)

(52) U.S. Cl.
CPC .............. *A61B 8/065* (2013.01); *A61B 8/461* (2013.01); *A61B 8/488* (2013.01); *A61B 8/5223* (2013.01); *A61M 2205/3375* (2013.01)

(58) Field of Classification Search
CPC ................................ A61B 8/065; A61B 8/461
USPC ........................................................ 600/437
See application file for complete search history.

(56) References Cited

U.S. PATENT DOCUMENTS

| | | | |
|---|---|---|---|
| 2012/0197118 A1* | 8/2012 | Lisiecki | A61B 8/04 600/438 |
| 2013/0303915 A1* | 11/2013 | Barnard | A61B 8/461 600/449 |
| 2014/0278478 A1* | 9/2014 | Vezina | A61B 5/0006 705/2 |

* cited by examiner

*Primary Examiner* — Nicole F Lavert
*Assistant Examiner* — Nicole F Johnson
(74) *Attorney, Agent, or Firm* — Whiteford, Taylor & Preston, LLP; Gregory M. Stone (57) ABSTRACT

Disclosed are systems and methods using ultrasound to predict if a patient's cardiac stroke volume will increase with a fluid bolus. Ultrasound measures are taken before administering a fluid bolus, including measurement of the left ventricular outflow tract velocity time integral (LVOT VTI), and venous measurements of the internal jugular vein. Data collected from such ultrasound scan is then used to predict the patient's cardiac volume response in the event that a fluid bolus is administered to that patient.

7 Claims, 5 Drawing Sheets

| | Measure | Assessment | Mode | Difficulty |
|---|---|---|---|---|
| VTI | Outflow through the aortic valve | Outflow LV | Doppler | +++ |
| 0-90° IJ | Positional change in the IJ diameter | Inflow RV | 2D | ++ |
| rv IJ 90° | Respiratory variation in the IJ at 90° | Inflow RV | 2D | + |
| rv SVV | Variation in stroke volume with respiration | Outflow LV | Doppler | ++++ |
| plr SVV | Variation in stroke volume with passive leg raise | Inflow RV/ Outflow LV | Doppler | ++++ |
| rv IVC | Respiratory variation in the IVC | Inflow IVC | 2D | ++ |

| | Measure | Assessment | Mode | Difficulty |
|---|---|---|---|---|
| VTI | Outflow through the aortic valve | Outflow LV | Doppler | +++ |
| 0-90° IJ | Positional change in the IJ diameter | Inflow RV | 2D | ++ |
| rv IJ 90° | Respiratory variation in the IJ at 90° | Inflow RV | 2D | + |
| rv SVV | Variation in stroke volume with respiration | Outflow LV | Doppler | ++++ |
| plr SVV | Variation in stroke volume with passive leg raise | Inflow RV/ Outflow LV | Doppler | ++++ |
| rv IVC | Respiratory variation in the IVC | Inflow IVC | 2D | ++ |

FIG. 1

| | (-VR) | (+VR) | % measurable | NPV/PPV |
|---|---|---|---|---|
| CAVS | ≤ 0.24 | > 0.40 | 73% | 70%/80% |
| VTI | ≥ 22 cm/sec | ≤ 18 cm/sec | 78% | 74%/70% |
| 0-90° IJ | ≤12% | ≥40% | 75% | 61%/64% |
| rv IJ 90° | <12% | ≥25 % | 79% | 71%/60% |
| rv SVV | <10% | ≥15% | 62% | 65%/67% |
| rv IVC | <10% | >50% | 65% | 53%/59% |

Non-Responder (-VR)

Non-Responder (+VR)

SYSTEM AND METHOD FOR ASSESSMENT OF CARDIAC STROKE VOLUME AND VOLUME RESPONSIVENESS

CROSS-REFERENCE TO RELATED APPLICATION

This application is a divisional of U.S. patent application Ser. No. 15/407,380 entitled "SYSTEM AND METHOD FOR ASSESSMENT OF CARDIAC STROKE VOLUME AND VOLUME RESPONSIVENESS," filed with the U.S. Patent and Trademark Office on Jan. 17, 2017, now U.S. Pat. No. 10,736,604, by the inventor herein, which is based upon and claims the benefit of U.S. Provisional Patent Application Serial No. 62/278,717 entitled "Combination Assessment of Volume Status (CAVS)," filed with the U.S. Patent and Trademark Office on Jan. 14, 2016 by the inventor herein, and of U.S. Provisional Patent Application Serial No. 62/443,276 entitled "Method for Estimation of Cardiac Stroke Volume (eSV) and Cardiac Output (eCO)," filed with the U.S. Patent and Trademark Office on Jan. 6, 2017, the specifications of which are incorporated herein by reference in their entireties.

STATEMENT OF GOVERNMENT SUPPORT

This invention was made with government support under Grant No. FA8650-13-2-6D10 awarded by the Air Force Office of Scientific Research. The Government has certain rights in the invention.

FIELD OF THE INVENTION

The present invention relates generally to clinical medical treatment of critically ill patients, and more particularly to systems and methods for assessing cardiac stroke volume in a patient, and to methods for predicting a patient's stroke volume response to a fluid bolus.

BACKGROUND OF THE INVENTION

Early and aggressive fluid resuscitation in patients suffering from shock is associated with improvement in outcome, including mortality. Multiple studies have supported this concept in a variety of clinical settings, from septic shock to high-risk surgical patients. However, a clear association also exists between cumulative fluid balance and mortality. It therefore becomes prudent to adopt a tailored approach to fluid resuscitation over empiric fluid loading. After all, a fluid bolus that does not lead to increased stroke volume is unlikely to benefit the patient, and carries all of the risk associated with volume overload.

Multiple methods, invasive or otherwise, have been proposed to predict an increase in cardiac stroke volume (referred to herein at times as SV) with a fluid bolus, or which increase in stroke volume is referred to as volume responsiveness (referred to herein at times as VR). Stroke volume (measured in ml/beat) is the amount of blood pumped out of the heart with each beat (and more specifically a cone of blood that comes through the left ventricular outflow tract (LVOT)). Stroke volume is also an important determinant of fluid status, and thus can be helpful in directing the administration of fluid boluses. While central venous pressure (CVP) has traditionally been used to assess volume status, studies have not demonstrated a reliable relationship between CVP and volume responsiveness. Pulmonary artery catheters (PAC) have also fallen out of favor due to their invasiveness and potential for serious complications. Several studies have failed to show any improvement in outcome associated with PAC use. Given its non-invasive nature, portability, and ease of use as a point-of-care test, ultrasound (US) has emerged as an attractive option to assess volume status and predict fluid responsiveness.

The most studied ultrasound measure is respiratory variation in the inferior vena cava (rvIVC). This measure is relatively easy to perform with any point-of-care ultrasound system. While multiple studies have demonstrated that rvIVC accurately predicts volume responsiveness in mechanically ventilated patients, there is conflicting evidence in spontaneously breathing patients. rvIVC measurement may be difficult or impossible to perform in many surgical patients, and particularly those presenting with abdominal distension, surgical wounds, morbid obesity, or bowel gas. Additionally, evidence suggests that in the setting of increased thoracic and abdominal pressures, IVC diameter and collapsibility indices may lose their reliability.

Given the varied and limited successes of prior known methods, which generally assess only one metric, it would be advantageous to provide more easily implemented system that allows several ultrasound metrics to be included in the measurements and predictions. This would allow healthcare providers to administer fluid only to those patients most likely to have a positive response, who have a low stroke volume to begin with and limiting application to those least likely to have a positive response (and thereby reducing the risk of volume overload in such patients). It would also be advantageous to provide systems and methods of using noninvasive ultrasound measurements to predict whether a given patient will be likely to have a positive volume response to a fluid bolus prior to its administration.

SUMMARY OF THE INVENTION

Disclosed herein are systems and methods for using ultrasound to predict volume responsiveness in critically ill surgical patients and those suffering from shock. In accordance with certain aspects of an embodiment of the invention, computer software applications are provided that support point-of-care ultrasound (POCUS) that perform one or more of (i) allowing physicians to more easily and accurately predict which patients will benefit from a fluid bolus, and (ii) simplifying and standardizing the measurement of stroke volume and cardiac output. Such software applications may include an interactive calculator useful for guiding fluid administration, use of vasopressors, and use of inotropic medications. Such computer software may be helpful in supporting clinical decision making, which the field has thus far seen little of by way of software application development. More particularly, to the knowledge of the inventor, there are no known currently available applications that allow for the POCUS-driven hemodynamic analysis discussed herein, and none of the known software packages offered on available ultrasound systems have the performance capabilities disclosed herein.

The systems and methods set forth herein allow for POCUS to be performed and interpreted by a healthcare provider, such as a treating physician, sonographer, echocardiologist, or radiologist, when evaluating patient volume responsiveness, allowing the healthcare provider to make related medical decisions based on test results faster than by a standard method of operation. When using a standard US system the healthcare provider orders an exam, the patient then goes to a different site, the US is performed by a sonographer, the results are interpreted by a cardiologist or radiologist, and a written report is generated and sent back to the treating physician.

The software operable with such prior known US systems is designed for this standard method of operation. That method is complex, cumbersome and does not provide data in a format designed to guide real-time clinical decision-making. Despite these challenges, the desire is growing to apply POCUS across a wide variety of aspects of medicine.

For instance, POCUS can be used anywhere, from outer space in the international space station to the remote corners of Brazil and Africa. The modality itself is rapid, safe, portable, and far less expensive than other imaging technology, such as CT. However, healthcare providers having minimal training with POCUS are using the system to make important decisions despite using US systems created for a different type of healthcare provider.

In accordance with certain aspects of the invention, methods, including computer-implemented methods, are provided that allow healthcare providers to more easily and accurately measure SV and to predict if the patient is likely to have a positive response to a fluid bolus, such that there is a likelihood that the patient's SV will increase with a fluid bolus. Such method was derived from a volume responsiveness study (discussed in detail below) that comprised an observational study of 138 patients receiving a fluid bolus. An echocardiogram was performed before and after the bolus, and patients who responded with an increase in SV were identified (+VR). Several ultrasound measures were taken before administering the fluid bolus, including an arterial measurement referred to as the left ventricular outflow tract velocity time integral (LVOT VTI) and venous measurements of the internal jugular vein.

Computer modeling was then used to determine the most predicative combination of variables, and the analytical and decision processes described herein were created using those variables. Both the patient's VTI and the patient's respiratory variation of the internal jugular were found to be particularly predictive, and their combined assessment even more so, of a patient's volume responsiveness. The training receiver operating curve (ROC) for accurately predicting+ VR was excellent at 0.90 (p<0.0001). Importantly, the model performed well with validation testing, maintaining an ROC of 0.77 (p<0.0001).

In accordance with further aspects of the invention, methods, including computer-implemented methods, are provided that streamline and simplify the way in which SV itself is assessed by estimating left ventricular outflow track diameter (eLVOTD) using patient characteristics including age, sex, height, weight, and body surface area. Left ventricular outflow tract diameter (LVOTD) is a determinant of stroke volume, discussed above, and of cardiac output (CO measured in L/min), both of which are typically derived by echocardiography (ultrasound of the heart). CO is the stroke volume (measured in mL/beat) multiplied by the heart rate (HR measured in beats/min), and as with stroke volume, is a valuable measure of cardiac function, and thus can help determine the need for inotropic support of the heart, especially if used with another echocardiographic measure. Also, in combination, mean arterial blood pressure (MAP measured in mmHg) and CO can be used to determine the systemic vascular resistance (SVR measured in dynes/cm$^2$), which may direct vasopressor use.

Stroke volume can be estimated using both the LVOTD and LV VTI. While the VTI has been found to be reliably assessed by ultrasound in more than 85% of patients, the inventor's clinical experience has shown that LVOTD can be very difficult to accurately measure. More particularly, preliminary data has indicated that reliable ultrasound images for determining LVOTD are only present in about 50% of the data reviewed. As a result, most POCUS cardiac evaluations are limited to simple qualitative assessments, including right ventricular function and left ventricular ejection fraction. Current state of the art for taking measurements of SV, CO, and SVR require an invasive hemodynamic monitor and a hospitalized setting.

In contrast, POCUS can be performed anywhere and is relatively risk free. Initial modeling using the methods set forth herein shows reasonable agreement between eLVOTD and measured LVOTD, with an RMSE of 0.15 and the $R^2$ of 0.74. Through use of the eLVOTD as discussed herein, SV and CO may be more easily and reliably assessed with POCUS. When such quantitative echocardiogram data is combined with qualitative RV and LV EF assessment, POCUS will provide a better hemodynamic assessment tool than currently exists.

BRIEF DESCRIPTION OF THE DRAWINGS

The numerous advantages of the present invention may be better understood by those skilled in the art by reference to the accompanying figures in which.

DETAILED DESCRIPTION OF THE PREFERRED EMBODIMENTS

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form. Further, it should be understood that the figures are not drawn to scale and in some instances details that are not necessary for the understanding of the present invention are omitted such as common methods of manufacturing.

In accordance with certain aspects of an embodiment of the invention, methods, including computer-implemented methods, are provided that allow healthcare providers to more easily and accurately predict if a patient's cardiac stroke volume will increase with a fluid bolus. According to one embodiment of the present invention, predicting the stroke volume responsiveness of a patient to a fluid bolus includes measuring the patient's respiratory variation of the internal jugular (rvIJ) and the patient's velocity time integral (VTI). A method and system, described below as combined assessment of volume status (CAVS) increases the accuracy of a healthcare provider's measurements and reduces the likelihood of risk to the patient.

To determine predicative factors capable of making such a prediction, patients admitted to an intensive care unit and receiving a fluid bolus or blood product transfusion for clinical indications were deemed eligible for enrollment in the study. After informed consent was obtained, patients underwent two transthoracic echocardiograms (TTE); one just prior to the bolus/transfusion (pre-TTE), and a second upon its completion (post-TTE). The stroke volume was assessed in both exams, and the percent change as a result of the fluid was calculated. Patients with an increase of ≥15% in the stroke volume were determined to be volume responsive (+VR). The predictive accuracy of several different ultrasonographic measures in assessing volume responsiveness were directly compared.

The relevant population was surveyed over a 36-month period, Monday-Friday from 7:00 a.m. to 4:00 p.m. Patients receiving crystalloid, colloid or blood product transfusion were identified. If the patient was able to consent, or the legally authorized representative of the patient was present, he or she was approached for enrollment. Administration of the fluid was not delayed for either enrollment or performance of the pre-TTE. Clinical data including demographic (age, sex, admission diagnosis) and clinical information (body surface area, mean arterial blood pressure, heart rate, 24 hour fluid balance) were extracted from the medical record. The ventilator settings and surgeries performed prior to the pre-TTE were recorded. The type and the type amount of the bolus was also noted.

All exams ire performed by a dedicated cardiac sonographer or trained surgical intensivist using a Phillips CX-50® ultrasound system (Andover, Mass., USA) with cardiac calculation package. For the cardiac measurements a phased array 3S cardiac transducer was used. For the internal jugular (IJ) vein assessment a high frequency linear transducer was employed. The pre-TTE was performed within thirty minutes of the fluid administration and the post within thirty minutes of its completion. Both exams were focused rapid echocardiographic exams (FREE) that includes four standard views: parasternal long axis (PLA), parasternal short axis (SA), apical (AP), and sub-xhyph od (SX). FREE is similar to a standard TTE, except that the measurements and interpretation are hemodynamically rather than anatomically oriented. Ejection fraction and diastolic function is assessed as part of the FREE. The internal jugular measurements described below were added to the pre-TTE as part of the analysis.

In both the pre- and post-TTE, the stroke volumes of a patient was assessed using pulsed-wave Doppler US through the left ventricular outflow tract (LVOT) from the AP window. The VTI and the left ventricular outflow tract diameter in the PLA was measured to calculate the patient's SV. If the patient was in atrial fibrillation, the average of 5 beats was taken. The patient was excluded from the study if the SV measurements could not be obtained because either the patient's VTI could not be measured due to anatomic reasons or aliasing was too high because of high velocity flow. The pre- and post-bolus VTI were recorded and the percent change in stroke volume was determined by the equation:

$$\text{Percent Change in SV} = ((\text{Post VTI} - \text{Pre VTI})/\text{Pre VTI})*100$$

Respiratory variation in the inferior vena cava (rvIVC) was then evaluated in M-mode. More particularly, the liver was identified from a sub-costal view. The IVC was located in long axis passing into the right atrium. A cursor was placed just proximal to the insertion of the hepatic veins, approximately 2 cm into the liver. M-mode was recorded over several respiratory cycles. The maximum and minimum diameter of the IVC was determined and recorded.

Similarly, the rvIVC was evaluated in 2D. As described above, the IVC was located in long axis. Rather than looking at the hepatic vein insertion, the entire IVC was assessed to determine if the patient had respiratory variation anywhere along the IVC. The maximum and minimum IVC measurements were obtained using a caliper. The percent change of IVC for both M-mode and 2D was determined quantitatively (as described below) and by simple visual assessment (e.g., indicating a yes or no change). The percent change of the IVC was determined by the difference of the maximum and minimum IVC diameters divided by the maximum IVC diameter.

Similar to the SV measurement, as described above, respiratory stroke volume variation (rSVV) was obtained from the AP window by using pulsed wave Doppler US. To determine the rSVV, the sweep speed was decreased to sample both the maximum and minimum VTI from one screen. The SVV measurements could not be performed if the patient was in atrial fibrillation (afib). The peak flow and minimum flow was determined and the rSVV was calculated using the equation:

$$\text{rSVV} = ((\text{max VTI} - \text{min VTI})/\text{max VTI})*100$$

Next, SV was evaluated with passive leg raise, in which the US transducer was placed at the apical window so that the VTI could be measured. The patient was supine (0 degrees), with their legs and head flat on the bed. Both of the patient's legs were raised from 45 degrees (45°) to an upright position of 90 degrees (90°), and the Vii was again recorded. The difference in with the patient's legs raised to the upright position was calculated.

Next, internal jugular vein (IJ) diameter was measured using a high frequency linear transducer. The left IJ was imaged in short and long axis, first with the patient in the supine position (0°), and again with the head of the patient's bed positioned in the upright position (i.e., at 90° to the patient's legs). By adjusting the head of the patient's bed, the patient's head was maintained in a neutral position while imaging the left IJ. The short axis view was taken in the mid-neck. For the long axis view, the transducer grove was aimed towards the patient's head. The maximum and minimum diameter of the patient's left U in the supine position (IJ 0° max and IJ 0° min, respectively) were measured from the short axis view, and the maximum and minimum diameter of the patient's left U in the upright position (IJ 90° max and IJ 90° min, respectively) were measured from the short axis view. The resulting supine and upright respiratory variations (rv IJ 0° and rv IJ 90°, respectively) and the change in cross sectional area were determined. Respiratory variation of positional change in the U was then calculated as follows:

| Respiratory variation 0° | (rv IJ 0°) | ((IJ 0° max − IJ 0° min)/IJ 0° max) × 100 |
| Respiratory variation 90° | (rv IJ 90°) | ((IJ 90° max − IJ 90° min)/IJ 90° max) × 100 |
| Positional IJ change | (pΔIJ) | ((IJ 0° − IJ 90°)/IJ 0°) × 100 |

Patients were separated into two groups based upon the above measurements: +VR (i.e. patients having a >15% increase in stroke volume with a fluid bolus) and −VR (i.e. patients not having a >15% increase in stroke volume with a fluid bolus).

A receiver operating characteristic (ROC) was used to determine threshold values for sensitivity and specificity. Standard ROC's determine a single threshold value that detects the most accurate single measurement. However, US is better understood as a semi-quantitive tool because estimates and ranges are generally more accurate forms of measurements than absolute measurements for the healthcare provider to use. To create a more useful clinical tool, the criterion and coordinate values of the ROC data were used to create upper and lower threshold values for the best sensitivity and specificity of each measurement below X the outcome is very unlikely, above Y the outcome is very likely, and between X and Y the outcome is indeterminate). The number of patients that had an indeterminate outcome was quantified. Logistic regression analysis was used to determine the most predictive combination of variables. The sensitivity and specificity of each measure were calculated using the threshold values. These analyses allowed a comparison of ranges between different measures.

Descriptive statistics were employed using a median with lower quartile and upper quartile (LQ-UQ) for continuous variables, and a number or percentage (%) for categorical variables. A probability of results being due to chance (P-value) of <0.05 was considered statistically significant.

A preliminary analysis determined that passive leg raise stroke volume variation could not be reliably measured and was not predictive of +VR. Differentiating stroke volume variation secondary to respiration from stroke volume variation resulting from raising the legs to the upright position was very difficult. It was also very difficult to determine when to measure the waveform after the patient's legs were raised to the upright position because many of the patients had anatomic limitations (e.g., femur or pelvic fractures), and movement of the lower extremities frequently caused the patients discomfort. As a result, the passive leg raise SVV measure was considered less preferable for predicting stroke volume responsiveness than the other measures, which were proved feasible. Upon completion, the IVC was assessed in 78% of patients, the SVV was assessed in 87% of patients, and the IJ was assessed in 90% of patients.

Figure 1:
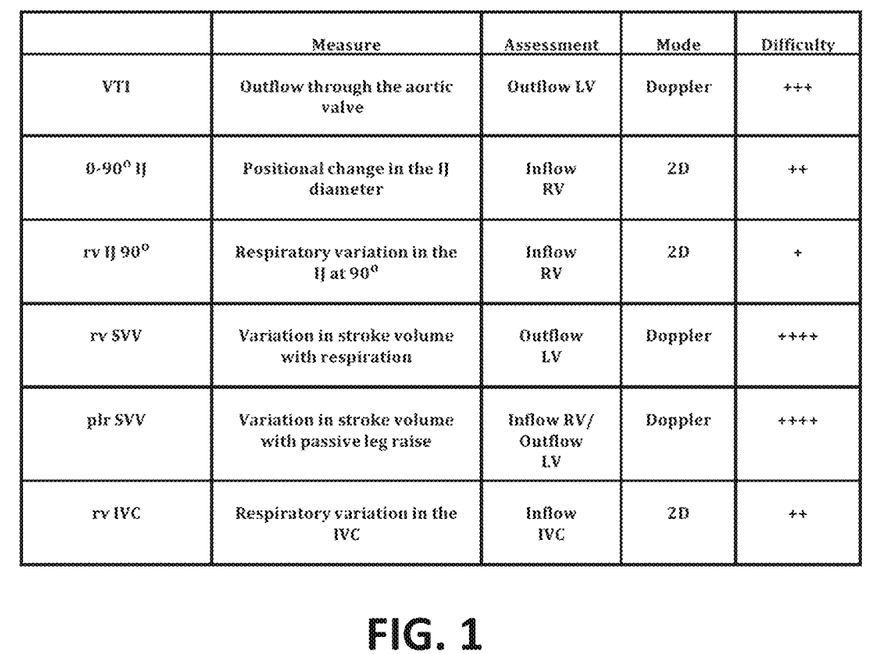
FIG. 1 is a chart summarizing each of the ultrasound measures of volume responsiveness considered as having potential value as a predictor of volume responsiveness.
Figure 2:
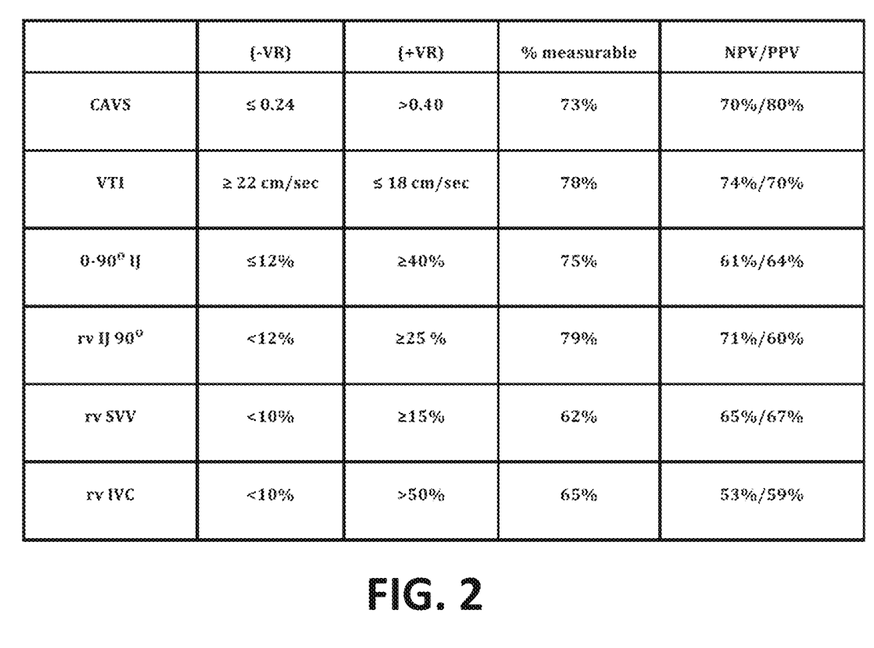
FIG. 2 is a chart reflecting values of each potentially predictive measure that is able to predict +VR or −VR in the measurable percentage of patients, including a negative predictive value and a positive predictive value.

FIG. 1 is a chart summarizing each of the ultrasound measures of volume responsiveness considered as having potential value as a predictor of volume responsiveness. In FIG. 1, the left column provides an abbreviation of the particular measure, followed by the definition of that measure, what metric the measure is used to assess, the ultrasound mode in which it is measured, and finally how difficult the measure is to perform. Likewise, FIG. 2 is a chart reflecting values of each potentially predictive measure that is able to predict +VR or −VR in the "% measurable" percentage of patients. In FIG. 2, the left column provides the metric, followed by threshold values for −VR and +VR, the percent of patients in whom the metric could be measured, and the negative and positive predictive values for each of the measures noted in the chart, namely, combination assessment of volume status (CAVS as discussed below), velocity time interval (VTI), variations in the diameter of the internal jugular (IJ) from a change in position, respiratory variation (rv IJ 90°) in the internal jugular, respiratory variation in stroke volume variation (rvSVV), and respiratory variation in the inferior vena cava (rvIVC). The threshold values for +VR define a positive fluid bolus responsiveness value range, and vary from metric to metric (some being equal to and greater than a particular value, and some being equal to and less than a particular value). As set forth in the chart of FIG. 2, the negative predictive value is the likelihood that a negative result will identify a patient who will not respond to a fluid bolus with an increase in SV whereas the positive predictive value is the likelihood that a positive result will correctly identify a patient who's SV does increase.

37% of the final population of patients were calculated as +VR, and 63% of the final population of patients were calculated as −VR. Pre-bolus ejection fraction and diastolic function were found to not have an effect on VR. Of the measures, pre-bolus VTI (p<0.001) and IJ measures (rv IJ 0° and pΔIJ; p<0.001 and) were found to be most significantly predictive of an increase in stroke volume with a fluid bolus.

Figure 3A:
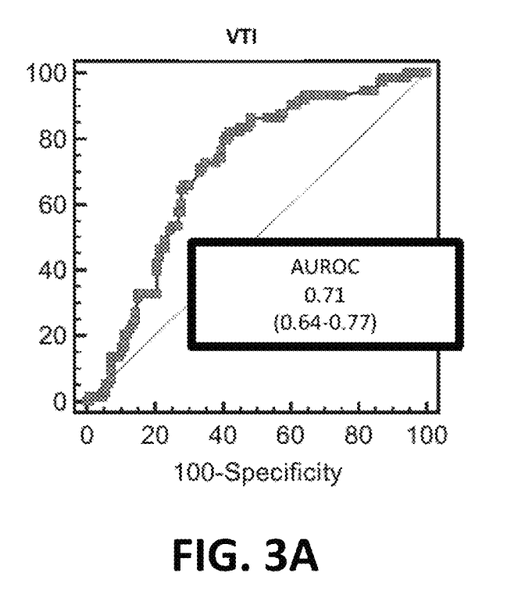
FIG. 3A is a graph illustrating pre-bolus VTI alone as a predictive measure of volume responsiveness.

A measure of pre-bolus stroke volume (pre-bolus VTI) was the single roost predictive measure of volume responsiveness. The area under the ROC (AUROC) curve was 0.71 (95% CI 0.64-0.77). Examination of the ROC showed the best threshold value is ≥22 cm to detect non-responders (i.e., −VR), and ≤18 cm to detect responsive patients (i.e. +VR). This allowed assessment in 78% of patients with a sensitivity of 75% and specificity of 70%. FIG. 3A shows a graph of pre-bolus VTI as a predictive measure of volume responsiveness, and particularly the accuracy of the VII alone to predict VR. The AUROC shows sensitivity (y-axis) graphed against specificity (x-axis), demonstrating the accuracy of the measure to determine both −VR and +VR.

Figure 3B:
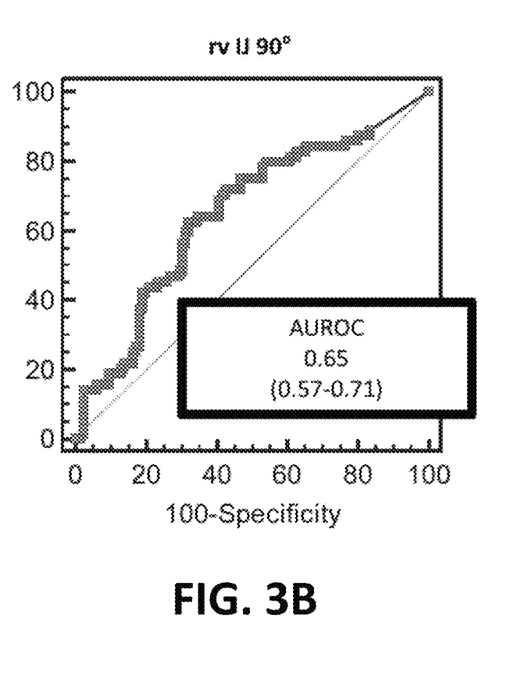
FIG. 3B is a graph illustrating; rv IJ as a predictive measure of volume responsiveness.

Further, respiratory variation in the internal jugular with the patient in the upright position (patient's head positioned at 90° to their legs, i.e. rv IJ 90°) was likewise found to be a significantly predictive measure of volume responsiveness. However, the AUROC for this measure was only 0.65 (95% CI 0.57-0.71). Examination of the ROC for rv IJ 90° showed the best threshold value is less than 12% change in diameter to detect non-responders (i.e. −VR), and at least 25% change in diameter to detect responders (i.e. +VR). FIG. 3B shows rv IJ 90° as a predictive measure of volume responsiveness, and particularly the accuracy of rv IJ 90° alone to predict VR.

Figure 4A:
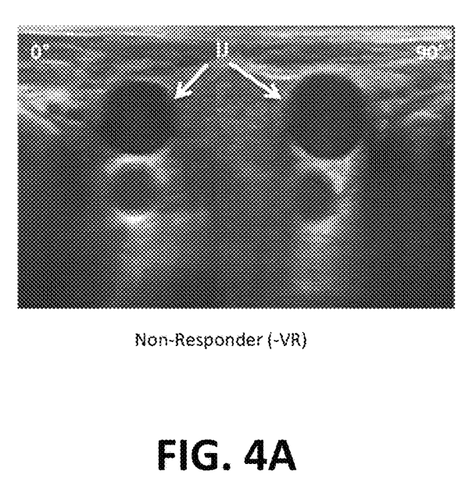
FIG. 4A is a pair of images showing scans of a patient's internal jugular vein taken when the patient was lying flat (0°) and sitting upright (90°) in a patient that did not respond to a fluid bolus, as shown by no change in the diameter of the internal jugular.
Figure 4B:
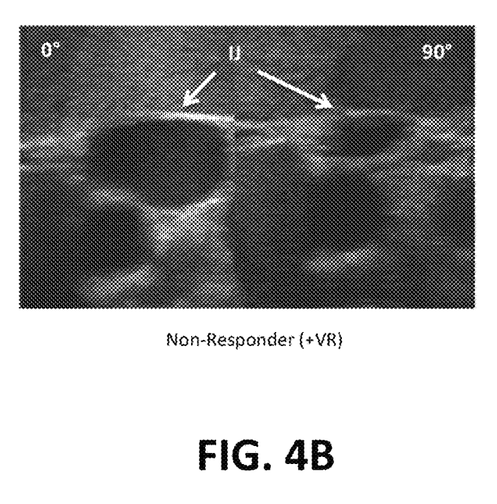
FIG. 4B is a pair of images showing scans of a patient's internal jugular vein taken when the patient was lying flat (0°) and sitting upright (90°) in a patient that did respond to a fluid bolus, as shown by a significant decrease in the diameter of the internal jugular.

Still further, positional variation of the internal jugular (0-90° IJ) also appeared to be a predictor of volume responsiveness, though with a still lower AUROC of 0.61 (95% CI 0.54-0.69). Examination of the ROC for 0-90° IJ showed the best threshold value is at most 12% change in diameter to detect non-responders (i.e. −VR), and at least 40% change in diameter to detect responders (i.e. +VR). FIGS. 4A and 4B provide images of scans of patient's internal jugular vein. FIG. 4A shows a pair of images showing the internal jugular above the carotid artery of a patient, taken when the patient was in the supine position (0°) and the upright position (90°) in a patient that did not respond to a fluid bolus, reflected by no change in the diameter of the internal jugular. Likewise, FIG. 4B shows a pair of images of a patient's internal jugular above the carotid artery taken when the patient was in the supine position (0°) and in the upright position (90°) in a patient that did respond to a fluid bolus, reflected by a significant decrease in the diameter of the internal jugular.

Figure 5:
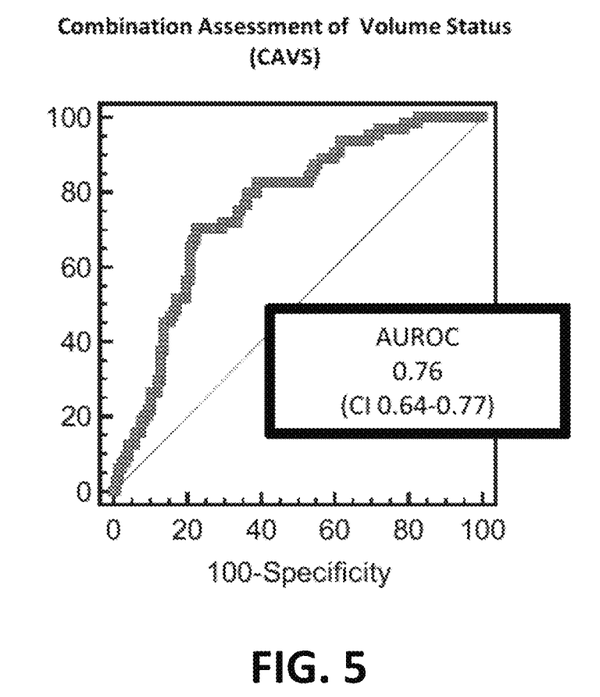
FIG. 5 is a graph illustrating combination assessment of volume status as a predictive measure of volume responsiveness.
Figure 6:
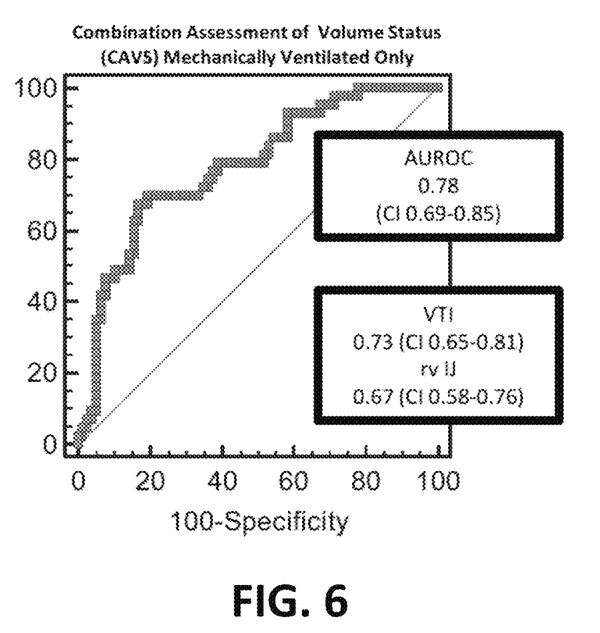
FIG. 6 is a graph illustrating combination assessment of volume status as a predictive measure of volume responsiveness in mechanically ventilated patients.
Figure 7:
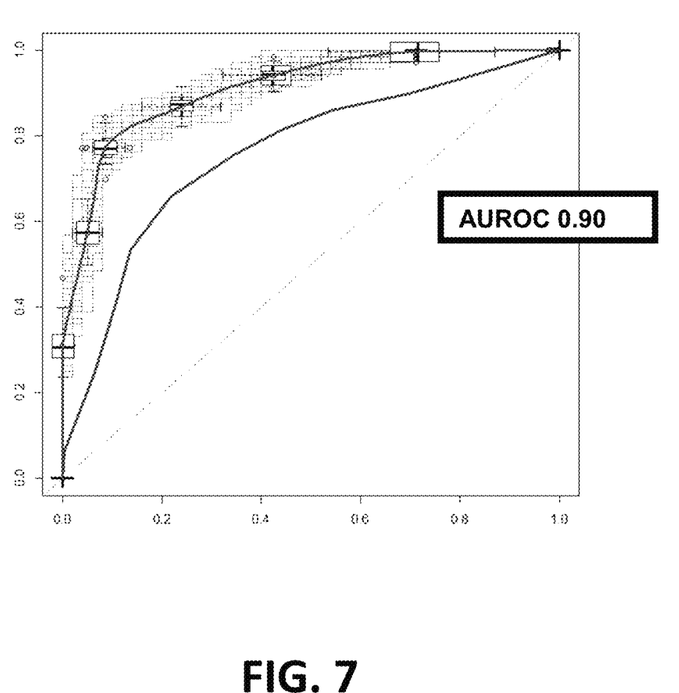
FIG. 7 illustrates one embodiment in accordance with the method described herein of combining several of the metrics as described to increase the AUROC to 0.90.

Importantly, when the rv IJ and the VTI were considered together, referred to at times herein as combined assessment of volume status (CAVS), the accuracy increased with a resultant AUROC of 0.76 (95% CI 0.69-0.82), FIG. 5 shows CAVS as a predictive measure of volume responsiveness, and more particularly an increase in the AUROC when VTI and IJ are combined. Likewise, when only mechanically ventilated patients were considered, all of the measures were found to be more accurate. FIG. 6 shows CAVS as a predictive measure of volume responsiveness in mechanically ventilated patients. FIG. 7 demonstrates the current method of combining several of the metrics as described. The AUROC rises to 0.90 when this is done.

Based on the foregoing predictive measures of volume responsiveness, and more particularly on the values of those factors that may be used to estimate the SV and CO and to predict +VR and −VR, computer software applications, including applications executable on US devices, personal computers, laptops, tablets, mobile devices, or any other computing devices may be provided that employ such values in analytical algorithms to receive the relevant data from an ultrasound transducer, to use the values noted above to determine whether a given patient is predicted to be +VR or −VR, and to provide output to a user of the software, such as the treating healthcare provider, that indicates the resultant prediction.

In a particular configuration, such software may specifically instruct the healthcare provider to administer a fluid bolus if the software has determined that the patient, based upon the collected ultrasound data, is predicted to be +VR. Likewise, in a particular configuration, such devices operating such software may automatically administer (such as by way of issuing a control signal to an intraveneous pump or other device) a fluid bolus to the patient, again if devices operating the software has determined that the patient, based upon the collected ultrasound data, is predicted to be +VR. The software receives as input pertinent demographic data (e.g., patient age, sex, height, and weight), clinical data (e.g., heart rate, systolic and diastolic blood pressure, and mechanical ventilation), and echocardiographic information (left ventricular outflow tract, velocity time integral, and internal jugular vein diameter variation). In accordance with certain aspects of a particular embodiment, such data may be automatically communicated from the ultrasound transducer to the software upon its collection, such as (by way of non-limiting example) through a wireless data connection between the ultrasound transducer and a BLUETOOTH® or wireless network communication module on the computing device, or other such communication channel as may be readily apparent to those skilled in the art.

In accordance with further aspects of the invention, methods, including computer-implemented methods, are provided that streamline and simplify the way in which stroke volume itself is assessed by estimating left ventricular outflow track diameter (eLVOTD) using patient characteristics including age, sex, height, weight, and body surface area of the patient. This provides a far less invasive method of determining a patient's cardiac output and stroke volume than currently implemented methods (i.e. placement of a pulmonary artery catheter (PAC) in the patient's heart), and more particularly allows for an accurate and reproducible echocardiographic calculation of cardiac output and stroke volume.

In order to estimate a patient's LVOTD, given the five variables of age, sex, height, weight, and body surface area, a design matrix $\Phi$ is constructed of N study cases by $$\Phi = (\phi(x_1), \phi(x_2), \ldots, \phi(x_N))^T, \text{ where}$$

$$\phi(x_i) = k(x, x_i) = \exp\left(-\frac{\|x - x_i\|^2}{2\sigma^2}\right),$$

namely a radial basis kernel function. The indice i is selected as a subset with 19 elements from the N cases. Let $y^{est}$ stand for estimated LVOT, and x stand for the input variable vector [age, sex, height, weight, BSA]. The variable $y^{train}$ stands for a vector of known LVOT values from N study cases. The estimation of LVOT is calculated by $$y^{est} = \beta(A + \beta\Phi^T\Phi)^{-1}\Phi^T y^{train})^T \phi(x^{new}),$$

where $\beta$ is the precision, A is a diagonal matrix which has its diagonal elements as ([1.8889, 1.2808, 0.2040, 0.9562, 0.7816, 1.4284, 1.8667, 0.4921, 0.4915, 1.4424, −0.4183, 1.5402, −2.2315, 1.7672, 0.6347, 0.9039, 0.6460, 1.2622, 1.3778]), and all other elements are zeros.

Through such estimation of the patient's LVOT, the healthcare provider using a device operating the software employing the foregoing method may input clinical and echocardiographic data and be able to derive important hemodynamic information, including cardiac output and stroke volume. According to some aspects, cardiac output is used in conjunction with the mean arterial blood pressure to calculate the systemic vascular resistance, and stroke volume is the most important measure of a patient's responsiveness of volume status, such as the patient's responsiveness to a fluid bolus. Taken together, the system and method as described herein increase the healthcare provider's ability to make better decisions about introphic, vasopressor and volume management in acutely ill patients than traditional methods.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It should be understood, therefore, that the invention may be practiced otherwise than as specifically set forth herein.

What is claimed is:

1. A system for predicting cardiac stroke volume responsiveness in a patient, comprising:
    an ultrasound transducer; and
    a computer processor in data communication with said ultrasound transducer, said computer processor having computer executable code stored thereon configured to:
        in response to receiving signals from said ultrasound transducer, detect a change in a patient's physiology corresponding to at least one of a change of inflow into a right ventricle of said patient and a change of outflow from a left ventricle of said patient, wherein said detection of said change in a patient's physiology further comprises at least one of (i) determining a maximum and minimum diameter of an internal jugular vein of said patient resulting from moving the patient from a supine position to an upright, seated position, and (ii) determining a maximum and minimum diameter of an inferior vena cava of said patient resulting from respiratory variation;
        determine whether said detected change is within a predetermined positive fluid bolus responsiveness value range; and
        in response to determining that said change is within said predetermined positive fluid bolus responsiveness value range, produce a human-readable output indicating that said patient has a likelihood of positive cardiac stroke volume response to a fluid bolus to be administered to said patient.

2. The system of claim 1, further comprising a mobile computing device in data communication with said computer processor, said mobile computing device having computer executable code stored thereon configured to display said human-readable output.

3. A method for predicting cardiac stroke volume responsiveness in a patient, comprising:
    providing an ultrasound transducer;
    providing a computer processor in data communication with said ultrasound transducer;
    receiving at said processor signals from said ultrasound transducer;
    in response to receiving said signals from said ultrasound transducer, detecting at said computer processor a change in a patient's physiology corresponding to at least one of a change of inflow into a right ventricle of said patient and a change of outflow from a left ventricle of said patient, wherein said detection of said change in a patient's physiology further comprises at least one of (i) determining a maximum and minimum diameter of an internal jugular vein of said patient resulting from moving the patient from a supine position to an upright, seated position, and (ii) determining a maximum and minimum diameter of an inferior vena cava of said patient resulting from respiratory variation;
    determining at said computer processor whether said detected change is within a predetermined positive fluid bolus responsiveness value range; and
    in response to determining that said change is within said predetermined positive fluid bolus responsiveness value range, producing at said computer processor a human-readable output indicating that said patient has a likelihood of positive cardiac stroke volume response to a fluid bolus administered to said patient.

4. The method of claim 3, further comprising the steps of:
    providing a mobile computing device in data communication with said computer processor; and
    displaying at said mobile computing device said human-readable output.

5. A method for administering a fluid bolus to a patient, comprising:
    providing an ultrasound transducer;
    providing a computer processor in data communication with said ultrasound transducer;
    receiving at said processor signals from said ultrasound transducer;
    in response to receiving said signals from said ultrasound transducer, detecting at said computer processor a change in a patient's physiology corresponding to at least one of a change of inflow into a right ventricle of said patient and a change of outflow from a left ventricle of said patient, wherein said detection of said change in a patient's physiology further comprises at least one of (i) determining a maximum and minimum diameter of an internal jugular vein of said patient resulting from moving the patient from a supine position to an upright, seated position, and (ii) determining a maximum and minimum diameter of an inferior vena cava of said patient resulting from respiratory variation;
    determining at said computer processor whether said detected change is within a predetermined positive fluid bolus responsiveness value range;
    in response to determining that said change is within said predetermined positive fluid bolus responsiveness value range, administering a fluid bolus to said patient.

6. The method of claim 5, further comprising the step of:
    in response to determining that said change is within said predetermined positive fluid bolus responsiveness value range, producing at said computer processor a human-readable output indicating that said patient has a likelihood of positive cardiac stroke volume response to a fluid bolus administered to said patient.

7. The method of claim 5, further comprising the steps of:
    providing a mobile computing device in data communication with said computer processor; and
    displaying at said mobile computing device said human-readable output.

* * * * *